United States Patent
Eikelmann et al.

(10) Patent No.: US 9,511,183 B2
(45) Date of Patent: Dec. 6, 2016

(54) FILLING AND RECIRCULATION DEVICE FOR A LIQUID SYSTEM OF AN EXTRACORPOREAL BLOOD TREATMENT DEVICE

(71) Applicant: B. BRAUN AVITUM AG, Melsungen (DE)

(72) Inventors: Guido Eikelmann, Baunatal (DE); Rainer Hector, Osnabrueck (DE)

(73) Assignee: B. BRAUN AVITUM AG, Melsungen (DE)

(*) Notice: Subject to any disclaimer, the term of this patent is extended or adjusted under 35 U.S.C. 154(b) by 0 days.

(21) Appl. No.: 14/783,266

(22) PCT Filed: Apr. 16, 2014

(86) PCT No.: PCT/EP2014/057744
§ 371 (c)(1),
(2) Date: Oct. 8, 2015

(87) PCT Pub. No.: WO2014/170378
PCT Pub. Date: Oct. 23, 2014

(65) Prior Publication Data
US 2016/0067400 A1     Mar. 10, 2016

(30) Foreign Application Priority Data
Apr. 19, 2013   (DE) .......... 10 2013 103 986

(51) Int. Cl.
*A61M 39/00* (2006.01)
*A61M 1/36* (2006.01)
(Continued)

(52) U.S. Cl.
CPC .......... *A61M 1/3647* (2014.02); *A61M 1/367* (2013.01); *A61M 1/3643* (2013.01);
(Continued)

(58) Field of Classification Search
CPC .. A61M 1/3643; A61M 1/3647; A61M 1/367; A61M 39/223; A61M 2039/226; A61M 2039/229; F16K 11/02; F16K 11/072; F16K 11/0856; F16K 15/18; F16K 31/60
See application file for complete search history.

(56) References Cited

U.S. PATENT DOCUMENTS

| 3,827,601 A | 8/1974 | Magrath |
| 4,397,335 A | 8/1983 | Doblar |

(Continued)

FOREIGN PATENT DOCUMENTS

| CA | 2807013 | 2/2012 |
| CN | 1809393 | 7/2006 |

(Continued)

OTHER PUBLICATIONS

German Search Report for German Application No. 10 2013 103 986.3 mailed Oct. 16, 2013, including partial translation.
(Continued)

*Primary Examiner* — Tatyana Zalukaeva
*Assistant Examiner* — Benjamin Klein
(74) *Attorney, Agent, or Firm* — RatnerPrestia (57) ABSTRACT

Disclosed is a filling and recirculation device of a fluid conducting system for blood treatment which has a fluid connector and a three-dimensional four-way valve with a first valve plane on which an inlet connector for the fluid container, an arterial line connector, and a valve-internal coupling connector are arranged and a second valve plane on which an outlet connector and a venous line connector are arranged. The venous line connector is permanently connected with the valve-internal coupling connector. A manually operable valve rotary piston of the four-way valve has a first control section assigned to the first valve plane and a second control section assigned to the second valve plane.

13 Claims, 4 Drawing Sheets

(51) Int. Cl.
  *A61M 39/22* (2006.01)
  *F16K 11/02* (2006.01)
  *F16K 15/18* (2006.01)
  *F16K 31/60* (2006.01)
  *F16K 11/072* (2006.01)

(52) U.S. Cl.
  CPC ........... *A61M 39/223* (2013.01); *F16K 11/02* (2013.01); *F16K 11/072* (2013.01); *F16K 15/18* (2013.01); *F16K 31/60* (2013.01)

(56) References Cited

U.S. PATENT DOCUMENTS

| | | |
|---|---|---|
| 4,819,653 A | 4/1989 | Marks |
| 4,844,810 A | 7/1989 | Richalley |
| 5,259,961 A | 11/1993 | Eigendorf |
| 5,334,315 A | 8/1994 | Matkovich |
| 5,540,653 A | 7/1996 | Schock |
| 5,669,879 A | 9/1997 | Duer |
| 8,617,093 B2 | 12/2013 | Kopperschmidt et al. |
| 2003/0125673 A1 | 7/2003 | Houde |
| 2010/0191106 A1* | 7/2010 | Koyama ............. A61M 39/223 600/431 |
| 2011/0137224 A1 | 6/2011 | Ibragimov |
| 2011/0208128 A1 | 8/2011 | Wu |

FOREIGN PATENT DOCUMENTS

| | | |
|---|---|---|
| CN | 102458503 | 5/2012 |
| DE | 4208274 | 10/1993 |
| EP | 2158934 | 3/2010 |
| WO | 8806895 | 9/1988 |

OTHER PUBLICATIONS

International Search Report for International Application No. PCT/EP2014/057744 mailed Aug. 8, 2014.
International Search Report for International Application No. PCT/EP2014/057745 mailed Aug. 7, 2014.
International Search Report for International Application No. PCT/EP2014/057749 mailed Jul. 31, 2014.
Chinese Office Action and Search Report for CN 201480022287.6, with translation, dated May 25, 2016.

* cited by examiner

FILLING AND RECIRCULATION DEVICE
FOR A LIQUID SYSTEM OF AN
EXTRACORPOREAL BLOOD TREATMENT
DEVICE

CROSS REFERENCE TO RELATED
APPLICATIONS

This application is the U.S. national phase application of PCT International Application No. PCT/EP2014/057744 filed Apr. 16, 2014, which claims priority to German Patent Application No. DE 10 2013 103 986.3 filed Apr. 19, 2013, the contents of each application being incorporated by reference herein.

FIELD OF THE INVENTION

The invention in hand concerns the filling and recirculation device of a fluid conducting system and/or liquid system, in particular an extracorporeal blood treatment device, for example a dialysis or apheresis machine.

BACKGROUND OF THE INVENTION

The hydraulic system (blood-side fluid system) of a blood treatment device, for example a dialysis machine, has to be filled with fluid, for example an NaCl solution or another sterile physiological solution, before being connected up to a patient, in such a way that air pockets in the system that would be dangerous for a patient connected up to the fluids of the system are eliminated. Furthermore, the hydraulic system should be flushed with the filled-in fluid for a certain period of time in order to filter/wash out any contaminants, dirt particles, etc. that may have deposited in the system before the system is connected up to the patient. On an extracorporeal blood treatment device, these two procedures are performed in the scope of a filling —circulation cycle, which is again an object of the invention in hand.

In the state of the art, there are fluid containers preferably in the shape of plastic bags designed especially for extracorporeal blood treatment devices of this relevant type in order to enable, among others, the device functions as described above. These kind of fluid containers are also manufactured and sold by the applicant.

As a rule, such a fluid container has a fluid intake chamber and two, preferably closable, fluid connectors. On a first of the two connectors, an arterial line section, and on the second connector, a venous line section of the hydraulic system (fluid system or also referred to as fluid conducting system) of the extracorporeal blood treatment device can be connected. The fluid bag as well as the two line sections together constitute a circulation device of the extracorporeal blood treatment device.

For the fluid system filling process, first the arterial line section is connected to the first fluid connector of the bag, and after opening of the first fluid connector, the hydraulic system is filled. The venous line section of the system first remains open to the atmosphere or is connected to a drain, a container or a bag so that air inside the system can escape and be vented in the atmosphere. As soon as the filling process is completed, the venous line section is connected to the second fluid connector of the bag by way of reconnecting in order to circulate the fluid inside the hydraulic system of the extracorporeal blood treatment device for a certain period of time or a certain volume of flow through the bag chamber.

During this optional circulation process, the fluid flows through internal filtering devices of the system in which remaining air pockets are removed/filtered out with the fluid. If necessary, the venous line section of the hydraulic system can again be disconnected from the second fluid connector of the fluid bag and the fluid inside the hydraulic system can be flushed out again under constant supply of fluid from the container. As a rule, however, the arterial line section is disconnected from the fluid bag and connected to the patient so that the fluid contained in the blood hose system can be displaced and discharged by the blood. Then the venous line section can be connected up to the patient. Upon completion of the circulation process and the application of both line sections (venous and arterial) to the patient for treatment, the filling/circulation cycle preparing for patient treatment is completed.

The description above of the filling/circulation cycle of a hydraulic system/fluid conducting system of an extracorporeal blood treatment device (dialysis machine) known from the state of the art indicates that the fluid bag remains in the system circuit for the filling and circulation processes, i.e. that the fluid inside the system is circulated through the fluid bag and/or its fluid chamber. As a result, the fluid in the fluid bag may get contaminated. As a consequence, the fluid bag has to be replaced by a new fluid bag in each case and cannot be used for a later therapy phase, e.g. during re-infusion. As a result, the fluid bag for the filling/circulation cycle performed before is disposed of independently of its residual fill plane. It is obvious that this procedure results in the wasting of a large quantity of fluid in case of a high patient treatment number because the fluid content of a fluid bag can only be used (incompletely) for the filling/circulation cycle.

Furthermore, fluid bags with two connectors as custom-made products are more expensive than conventional fluid bags, for example NaCl bags/bottles, with only a single connector. For this reason, the filling and recirculation device described above does not only imply a waste of filling and flushing fluid, but also an increase in cost due to expensive disposable fluid bags.

Finally, the conduits of the extracorporeal fluid conducting system of the blood treatment device that have to be filled permanently have to be reconnected for the individual filling and recirculation steps. In other words, the arterial line first has to be coupled with the fluid container, and the venous line has to be disconnected so that the flushing procedure can be carried out. Then the venous line has to be coupled with the fluid container again so that recirculation can be performed. For the final further flushing process, the venous line is disconnected again. When, finally, the arterial line and the venous line are applied to the patient, both fluid connectors on the fluid container have to be closed to avoid uncontrolled draining of the fluid container. This indicates that the handling of the known filling and recirculation system is not especially user-friendly.

SUMMARY OF THE INVENTION

In view of these problems, the task of the invention in hand is to provide a class-specific filling and recirculation device of a fluid system, preferably an extracorporeal blood treatment device, and a filling and recirculation procedure, which can be operated more efficiently and thus more cost-efficiently as compared to the state of the art. Furthermore, a purpose of the invention in hand is to make available a fluid system equipped with the filling and recirculation device according to aspects of the invention, for example an extracorporeal blood treatment device, that can be operated in a simple manner and that enables the use of conventional fluid bottles (e.g. NaCl bottles) in order to reduce an error risk during the operation of the device as well.

This task is completed with a filling and recirculation device of a fluid system/liquid system, preferably an extracorporeal blood treatment device (dialysis, apheresis machine) of the independent claim. Advantageous embodiments of the invention are the object of sub-claims.

The basic idea of the invention in hand is to design the class-specific filling device of a fluid conducting system (means for filling a fluid conducting system), in particular an extracorporeal blood treatment system, in such a way that a conventional (price-effective) fluid container of a known design such as a conventional NaCl bottle or a suitable bag with a single puncturable/connectable connector can be used. The connector of this fluid container is realized with a single manually operable fluid blocking mechanism (means for blocking fluid flow) with which all filling and (re)circulation processed can be switched so that the arterial line and the venous line of the extracorporeal conducting system only have to be reconnected once in each case (to connect to the patient) for each treatment.

Accordingly, a filling and (re)circulation device of a fluid conducting system of an extracorporeal blood treatment device is proposed, which has a fluid container connector (means for connecting a fluid storing means) and a manually operable fluid blocking mechanism in the form of a three-dimensional four-way valve with a first valve plane on which an inlet connector for the fluid container, an arterial line connector as well as a valve-internal coupling connector are arranged, with a second valve plane on which an outlet connector as well as a venous line connector are arranged, which is permanently fluidically connected with a valve-internal coupling connector of the first plane, and with a manually operable valve rotary piston which has a first piston control section assigned to the first valve plane and an axially spaced second piston control section assigned to the second valve plane, which are geared to each other in such a way that:
  a. in a valve piston rotary position for flushing, the first piston control section connects the inlet connector with the arterial line connector and the second piston control section connects the venous line section with the outlet connector;
  b. in a valve piston rotary position for (re)circulation, the first piston control section connects the valve-internal coupling connector with the arterial connector and the second piston control section disconnects the outlet connector from the venous valve connector; and
  c. in a valve piston rotary position for therapy, the first and the second piston control sections close off all connectors.

As a result of the arrangement of the fluid blocking mechanism according to aspects of the invention on the fluid container connector, it can remain on the conventional medical fluid container, preferably after puncturing of the container seal, whereas the arterial line section and the venous line section remain connected to the fluid blocking mechanism for a filling and (re)circulation process of the fluid conducting system and then can be disconnected again from the fluid blocking mechanism only afterwards without losing any fluid from the medical fluid container. Consequently the arterial line and the venous line require no reconnecting between the filling and (re) circulation process.

As the arterial line section and the venous line section can furthermore be disconnected from the connectors of the fluid blocking mechanism (e.g. Luer-Lock fitting), the arterial line section and the venous line section can be connected to an arterial and venous patient access directly after filling and (re)circulation without requiring any changes on the arterial line section and the venous line section and/or their connectors. This simplifies the handling of the filling and (re)circulation device according to aspects of the invention.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

According to FIG. 1, an extracorporeal blood treatment device 1, for example a dialysis or apheresis machine, has a hydraulic conducting system (hereinafter referred to as fluid conducting system) through which during a treatment phase on the machine side, for example, a blood purification fluid (dialysis fluid) is passed, and on the patient side, blood flows through it extracorporeally, whereby the machine-side and the patient-side fluid conducting systems are fluidically separated in case of a dialysis machine by a dialyser (filter) that is not shown in more detail. For this purpose, the (blood-bearing) fluid conducting system has a venous line section and an arterial line 2, 4 on the patient side, preferably with connectors (Luer-Lock fittings) 6, 8 on each hose section arranged/formed on the ends in each case to which, for example, injection needles or cannulas (not depicted) can be connected as patient access, which can be introduced in a patient's body.

In order to avoid a possibly necessary washing out of possible contaminations resulting from manufacturing in the patient's body, the extracorporeal blood treatment device 1 has a filling and (re) circulation device which enables a filling and circulation process in the present case, with which the patient-side fluid conducting system is cleaned as a rule before every patient treatment.

Figure 1:
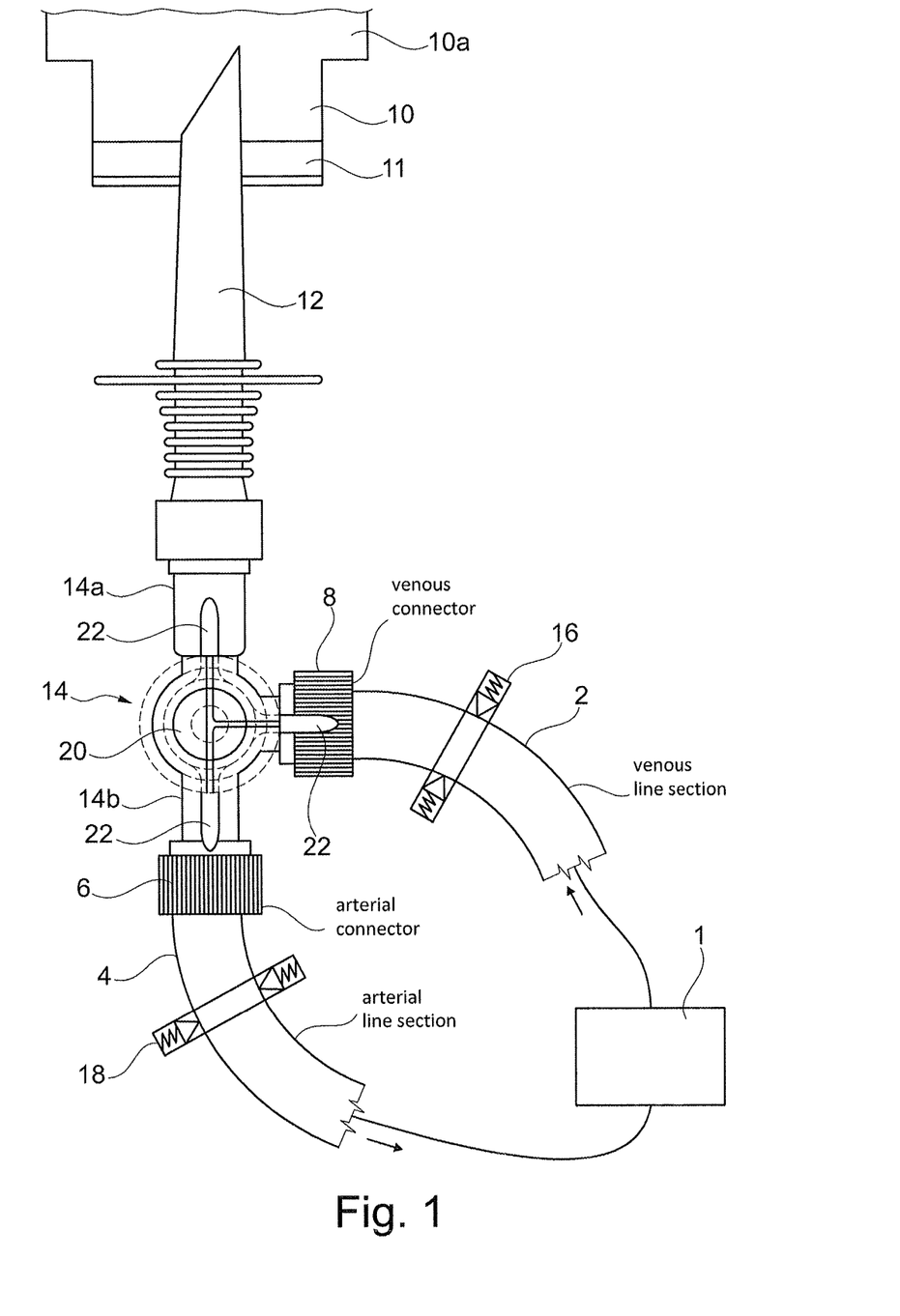
FIG. 1 shows a fluid system, preferably in the form of a circulation device, of an extracorporeal blood treatment device (dialysis machine) according to a preferred exemplary embodiment of the invention.

According to FIG. 1, the filling/recirculation device (or also filling/circulation device) according to aspects of the invention in hand has a fluid source, preferably in the form of a universal fluid container (NaCl bottle/bag) 10, with a single outlet 11 which is punctured in the exemplary embodiment in hand with a spike 12 as fluid container connector of the filling/recirculation device in order to tap fluid from the fluid container 10. The design of spike 12 matches known spike structures so that its design does not have to be explained in more detail here. Furthermore, it is to be pointed out that, for example, in case of a Luer-Lock or another fitting on the container side, the spike may replaced by a suitable connecting piece on the side of the filling/recirculation device. Furthermore, the filling/recirculation device according to aspects of the invention has a fluid blocking mechanism in the shape of a three-dimensional 4-way outlet or also a 4-way valve 14, which is arranged (directly) downstream of the spike 12 (connecting piece) in the direction of flow away from the fluid container 10.

In the case in hand, the spike 12 is directly (without interposition of an additional line section) connected to the 4-way valve 14. As an alternative, the spike 12 can also be realised in one piece or as a modular unit with the 4-way valve 14. The spike 12 can also be connected to the valve 14 with a connecting line section, whereby an additional non-return valve can be arranged between spike and valve, which blocks a flow in the direction of the fluid container 10.

Figure 2:
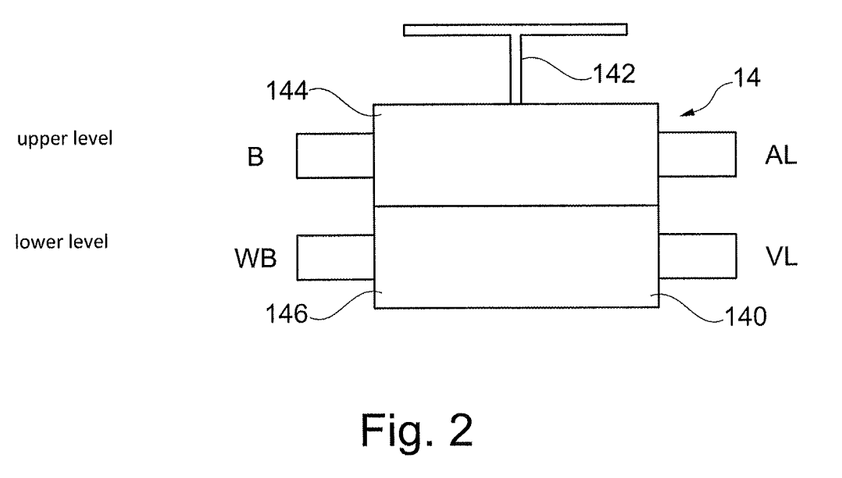
FIG. 2 shows the manually operable fluid blocking mechanism according to aspects of the invention in hand as a schematic diagram.

The three-dimensional 4-way valve 14 according to FIG. 2 has a cylindrical housing 140 in which a manually rotary valve piston 142 is inserted axially. The valve housing 140 constitutes, in an upper axial valve section 144, a first valve plane on which an inlet connector B for the fluid container 10 and an arterial line connector AL are formed, which are arranged spaced in circumferential direction of the valve housing 140, preferably radially opposite. Furthermore, the valve housing 140 constitutes, in a bottom axial valve section 146, a second valve plane on which an outlet connector WB as well as a venous line connector VL are arranged, which are also arranged spaced in circumferential direction, preferably radially opposite. The connectors B, AL of the first valve plane 144 are staggered to the connectors WB, VL of the second valve plane 146 in circumferential direction.

On the first valve plane 144, furthermore a valve-internal coupling connector VI is formed, which is permanently fluidically connected with the venous line connector VL of the second valve plane 146 with an axial duct within the valve housing 140, which is not shown any further.

Finally the manually operable valve rotary piston 142 has a first axial piston control section 142a assigned to the first valve plane 144, and a second piston control section 142b, axially spaced from it, assigned to the second valve plane 146. In both piston control sections 142a, b, two radial through-hole bores that cross each other are formed, the courses and alignments of which are geared to each other in such a way that in a valve piston rotary position for flushing according to FIG. 3a, the first piston control section 142a connects the inlet connector B with the arterial line connector VA and the second piston control section 142b connects the venous line connector VL with the outlet connector WB; in a valve piston rotary position for (re)circulation according to FIG. 3b, the first piston control section 142a connects the valve-internal coupling connector VI with the arterial line connector AL and the second piston control section 14ab disconnects the outlet connector WB from the venous line connector VL, and in a valve piston rotary position for therapy according to FIG. 3c, the first and the second piston control sections 142a, b close off all connectors.

Figure 3A:
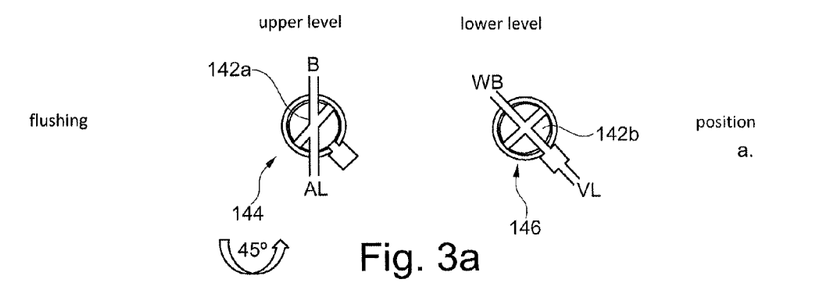
FIGS. 3a, 3b, 3c, 3d, and 3e show the switch positions of the fluid blocking mechanism according to aspects of the invention for the individual processes, in particular filling, (re)circulation and therapy processes, and optional patient connecting and conduit discharge processes.
Figure 3B:
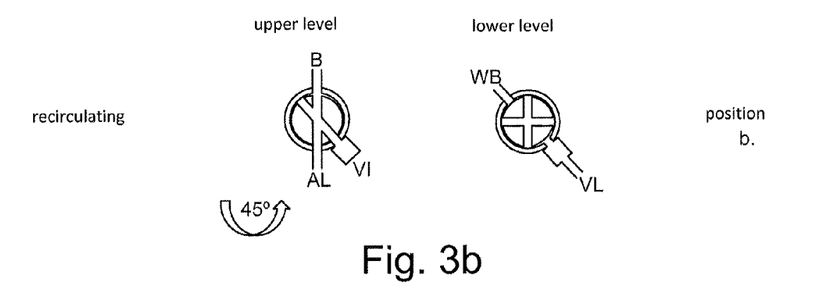
Figure 3C:
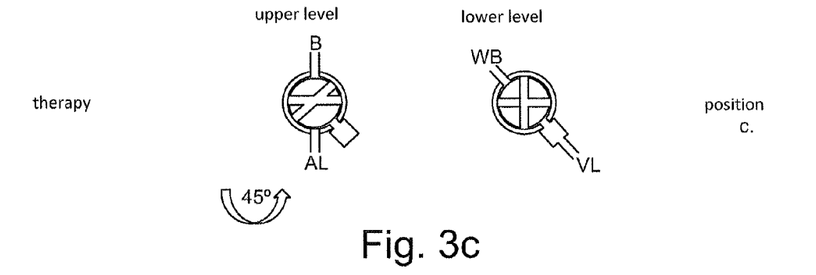
Figure 3D:
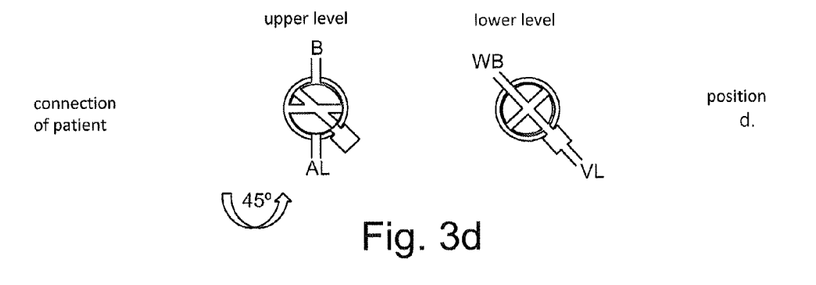
Figure 3E:
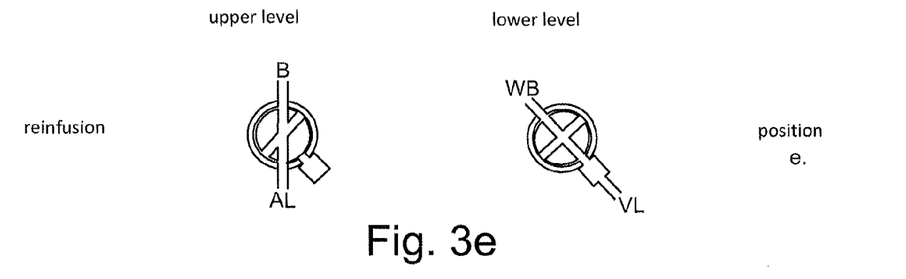

Furthermore, the two piston control sections 142a, b enable at least two further valve piston rotary positions, namely a valve rotary position for the process of connecting the arterial line and the venous line 2, 4 to a patient according to FIG. 3d, in which the first piston control section 142a disconnects the inlet connector B from the arterial line connector AL and the second piston control section 142b connects the venous line connector VL with the outlet connector WB, and a valve rotary position for the process of blood expulsion from the arterial line and the venous line 2, 4 in a patient according to FIG. 3e, in which the first piston control section 142a connects the inlet connector B with the arterial line connector AL and the second piston control section 142b connects the venous line connector VL with the outlet connector WB.

Finally, on the arterial line section and the venous line section 2, 4 according to FIG. 1, hose clamps 16, 18 are arranged in addition, which can be activated in particular for the process of connecting the blood-side conducting system of the blood treatment device to the patient in order to close the arterial line and the venous line 2, 4 and so to store the fluid contained in it after uncoupling from the 4-way valve 14 as well.

The function of the filling/recirculation device according to aspects of the invention is explained below based on FIG. 3a-e:

First the 4-way valve 14 remains in a valve shut-off position, for example according to FIG. 3c or 3e, in which at least the inlet connector B on the first valve plane 142a is closed. In this position, the valve 14 can be connected to the fluid container 10 without fluid running out of the container 10 in an uncontrolled manner.

Then the valve rotary piston 142 is rotated in the valve rotary position according to FIG. 3a (by approx. 45°) with which the arterial line and the venous line 2, 4 that were connected up before are serially connected with the fluid container 10 and can be filled with fluid. However, as the venous line 2 is connected with the outlet WB of the valve 14 in this position, a certain volume of fluid is flushed through the lines 2, 4, and takes along any contamination and air pockets contained in it in the process.

Then the valve rotary piston 142 is further rotated in the position according to FIG. 3b (by approx. 45°), in which the arterial and venous lines 2, 4 are short-circuited by way of the valve-internal coupling connector VI and the axial duct and a (re)circulation circuit is established in that way.

Figure 4A:
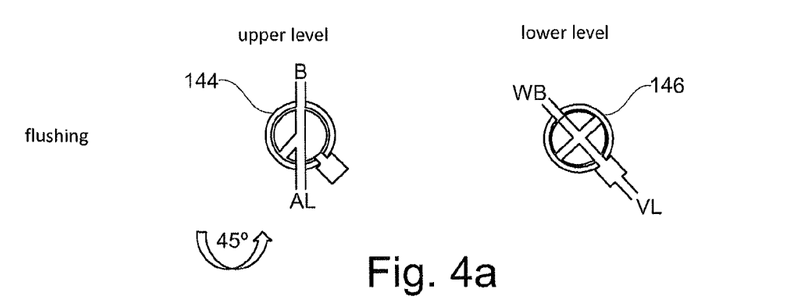
FIGS. 4a and 4b show alternative switch positions of the fluid blocking mechanism according to aspects of the invention for the individual processes "filling" and "(re)circulation".
Figure 4B:
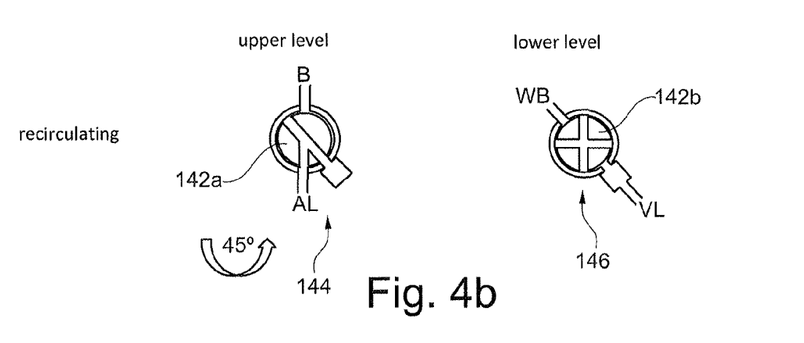

Here, it is to be pointed out that in this valve position, the fluid container 10 is still connected to the conducting system in order to supply more fluid as necessary. As an alternative to this, however, it can be provided according to FIGS. 4a and 4b that upon further rotating of the valve rotary piston 142 from the filling position (see FIG. 4a) in the recirculation position (see FIG. 4b), the fluid container is disconnected from the conducting system in order to avoid contamination of the container content in any case.

After recirculation, the valve rotary piston 142 is further rotated in a position according to FIG. 3d (by approx. 45°), in which the fluid container 10 is uncoupled. In this position, the venous line section 2 can remain connected with the valve outlet connector WB because the hose clamps 16, 18 were activated before in order to keep the filled-in fluid in the lines 2, 4. Now the arterial line and the venous line 2, 4 can be disconnected from the 4-way valve 14 and connected to the patient. First only the arterial line may be connected to the patient so that in the position shown in FIG. 3d, the fluid is displaced from the blood hose system by blood and is discharged through the outlet connector WB before the venous line is connected to the patient then. Then the valve rotary piston 142 is further rotated in the position according to FIG. 3c (by approx. 45°), in which all connectors of the 4-way valve are closed.

After therapy, there is still patient blood inside the extracorporeal conducting system, which has to be introduced into the patient again. For this purpose, only the arterial line 3 is first again connected to the 4-way valve 14 that is still closed, and the valve rotary piston 142 is further rotated in the rotary position according to FIG. 3e (by approx. 45°), whereby the fluid container 10 is connected with the arterial line 4 and the blood standing in the arterial and venous lines 2, 4 is returned into the patient's body. With that, the complete process is finished.

The invention claimed is:

1. Filling and recirculation device of a fluid conducting system of an extracorporeal blood treatment device comprising:
   a fluid container connector configured for connection with a single fluid connector of a medical fluid container; and
   a manually operable fluid blocking mechanism positioned downstream of the fluid container connector and configured to remain fluidically connected with the medical fluid container during the entire operation of the filling and recirculation device via the fluid container connector, the fluid blocking mechanism including:
   a three-dimensional four-way valve with a first valve plane on which an inlet connector for the medical fluid container, an arterial line connector, and a valve-internal coupling connector are arranged and a second valve plane on which an outlet connector and a venous line connector are arranged, the venous line connector permanently fluidically connected with the valve-internal coupling connector of the first plane; and
   a manually operable valve rotary piston including a first piston control section corresponding to the first valve plane and an axially spaced second piston control section corresponding to the second valve plane, the first and second piston control sections geared relative to each other such that:
   a. in a flushing valve piston rotary position, the first piston control section connects the inlet connector with the arterial line connector and the second piston control section connects the venous line section with the outlet connector;
   b. in a recirculation valve piston rotary position, the first piston control section connects the valve-internal coupling connector with the arterial connector and the second piston control section blocks the outlet connector from the venous line connector; and
   c. in a therapy valve piston rotary position, the first and the second piston control sections block all connectors.

2. Filling and recirculation device according to claim 1, wherein:
   d. in a patient connecting valve piston rotary position, the first piston control section blocks the inlet connector and the arterial connector and the second piston control section connects the venous line connector with the outlet connector.

3. Filling and recirculation device according to claim 2, wherein:
   e. in a re-infusion valve piston rotary position the first piston control section connects the inlet connector with the arterial line connector and the second piston control section connects the venous line connector with the outlet connector.

4. Filling and recirculation device according to claim 1, wherein:
   d. in a re-infusion valve piston rotary position the first piston control section connects the inlet connector with the arterial line connector and the second piston control section connects the venous line connector with the outlet connector.

5. Filling and recirculation device according to claim 1, wherein in the recirculation valve piston rotary position the first piston control section connects the inlet connector with the arterial line connector.

6. Filling and recirculation device according to claim 1, wherein in the recirculation valve piston rotary position the first piston control section blocks the inlet connector from the arterial line connector.

7. Procedure for performing a filling and recirculation process of a blood-side conducting system of a dialysis machine using a filling and recirculation device according to claim 1, comprising:
   connecting the fluid container connector to the single fluid connector of the medical fluid container with the four-way valve completely closed, and connecting the arterial line section and the venous line section, respectively, to the arterial and venous line connectors of the four-way valve while closed;
   flushing a fluid flow path along the arterial fluid line section and the venous line section of the extracorporeal blood treatment device by rotating the valve rotary piston from a valve shut-off position into the flushing valve piston rotary position;
   recirculating the fluid flow path by further rotating the valve rotary piston from the flushing valve piston rotary position into the recirculation valve piston rotary position; and
   connecting the fluid conducting system of the extracorporeal blood treatment device to a patient and performing a blood treatment after further rotating the valve rotary piston from the recirculation valve piston rotary position into the therapy valve piston rotary position.

8. Procedure for performing a filling and recirculation process according to claim 7, further comprising:
   draining the fluid conducting system of blood by further rotating the valve rotary piston from the therapy valve piston rotary position into a re-infusion valve piston rotary position in which the first piston control section connects the inlet connector with the arterial line connector and the second piston control section connects the venous line connector with the outlet connector.

9. Procedure for performing a filling and recirculation process according to claim 7, wherein connecting the fluid conducting system of the extracorporeal blood treatment device to a patient and performing a blood treatment comprises connecting first the arterial line section to the patient in order to have fluid inside the fluid conducting system displaced by blood, and then connecting the venous line section to the patient.

10. Procedure for performing a filling and recirculation process according to claim 7, wherein connecting the fluid conducting system of the extracorporeal blood treatment device to a patient and performing a blood treatment comprises disconnecting the four-way valve from the arterial line section after the valve rotary piston is further rotated into the patient connecting valve piston rotary position.

11. Procedure for performing a filling and recirculation process according to claim 7, wherein connecting the fluid conducting system of the extracorporeal blood treatment device to a patient and performing a blood treatment comprises disconnecting the four-way valve from the venous line section after the valve rotary piston is further rotated into the therapy valve piston rotary position.

12. Procedure for performing a filling and recirculation process according to claim 8, wherein draining the fluid conducting system comprises connecting the four-way valve to the fluid conducting system of the extracorporeal blood treatment device before the valve rotary piston is further rotated into the re-infusion valve rotary position.

13. A method of filling a blood-side fluid conducting system of a dialysis machine, the method comprising:
   the step of utilizing the filling and recirculation device according to claim 1.

\* \* \* \* \*